(12) United States Patent
Capetan

(10) Patent No.: US 6,398,789 B1
(45) Date of Patent: Jun. 4, 2002

(54) INTRAOCULAR LENS INJECTOR CARTRIDGE

(75) Inventor: Thomas G. Capetan, Fort Worth, TX (US)

(73) Assignee: Alcon Universal, Ltd., Hunenberg (CH)

(*) Notice: Subject to any disclaimer, the term of this patent is extended or adjusted under 35 U.S.C. 154(b) by 97 days.

(21) Appl. No.: 09/692,630

(22) Filed: Oct. 19, 2000

(51) Int. Cl.[7] .................................................. A61F 9/00
(52) U.S. Cl. ..................................................... 606/107
(58) Field of Search ........................ 606/107; 623/6.12, 623/907

(56) References Cited

U.S. PATENT DOCUMENTS

| 4,573,998 A | 3/1986 | Mazzocco |
| 4,681,102 A | 7/1987 | Bartell |
| 4,747,404 A | 5/1988 | Jampel et al. |
| 4,834,094 A | 5/1989 | Patton et al. |
| 4,836,201 A | 6/1989 | Patton et al. |
| 4,919,130 A | 4/1990 | Stoy et al. |
| 5,007,913 A | 4/1991 | Dulebohn et al. |
| 5,176,686 A * | 1/1993 | Poley .................... 606/107 |
| 5,190,552 A | 3/1993 | Kelman |
| 5,275,604 A | 1/1994 | Rheinish et al. |
| 5,304,182 A | 4/1994 | Rheinish et al. |
| 5,469,867 A | 11/1995 | Schmitt |
| 5,494,484 A | 2/1996 | Feingold |
| 5,496,328 A | 3/1996 | Nakajima |
| 5,499,987 A | 3/1996 | Feingold |
| 5,520,664 A * | 5/1996 | Bricault, Jr. et al. ........ 604/265 |
| 5,616,148 A | 4/1997 | Eagles et al. |
| 5,620,450 A | 4/1997 | Eagles et al. |
| 5,653,715 A | 8/1997 | Reich et al. |
| 5,653,753 A | 8/1997 | Brady et al. |
| 5,716,364 A | 2/1998 | Makker et al. |
| 5,735,858 A | 4/1998 | Makker et al. |
| 5,803,925 A | 9/1998 | Yang et al. |
| 5,826,584 A | 10/1998 | Schmitt |
| 5,947,976 A | 9/1999 | Van Noy et al. |
| 6,083,231 A | 7/2000 | Van Noy et al. |
| 6,143,001 A | 11/2000 | Brown et al. |

FOREIGN PATENT DOCUMENTS

| DE | 43 01 573 A | 7/1994 |
| EP | 0 962 195 A1 | 3/1999 |
| GB | 2224214 A | 5/1990 |
| WO | WO 9420027 | 9/1994 |
| WO | WO 96/29956 | 10/1996 |
| WO | WO 98/05281 A | 2/1998 |
| WO | WO 98/12969 A | 4/1998 |
| WO | WO 98/15244 | 4/1998 |
| WO | WO 00/62712 | 10/2000 |

* cited by examiner

Primary Examiner—Jeffrey A. Smith
(74) Attorney, Agent, or Firm—Jeffrey S. Schira

(57) ABSTRACT

An intraocular lens injector cartridge having a heat retention additive for helping the cartridge retain heat once the cartridge is warmed. Such additives can include an biocompatible material having high heat retention, for example, powdered gold.

4 Claims, 1 Drawing Sheet

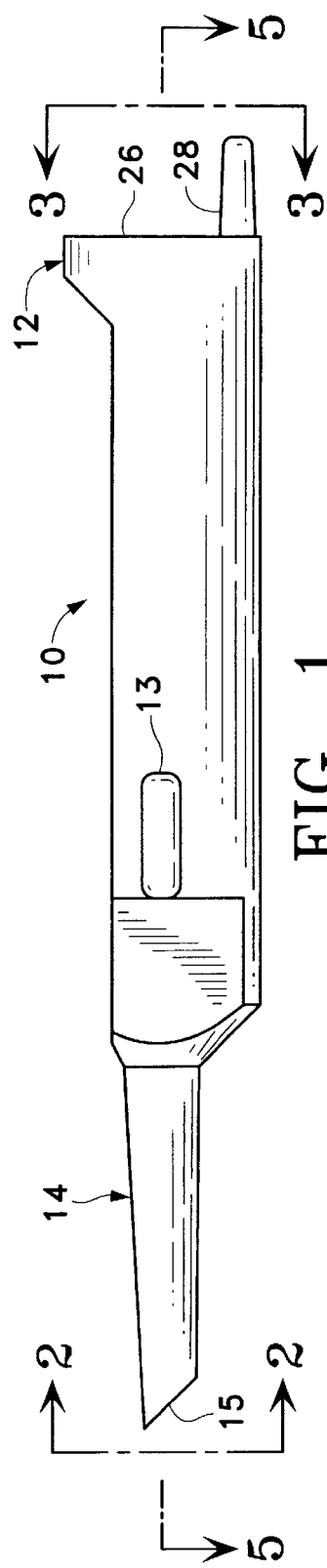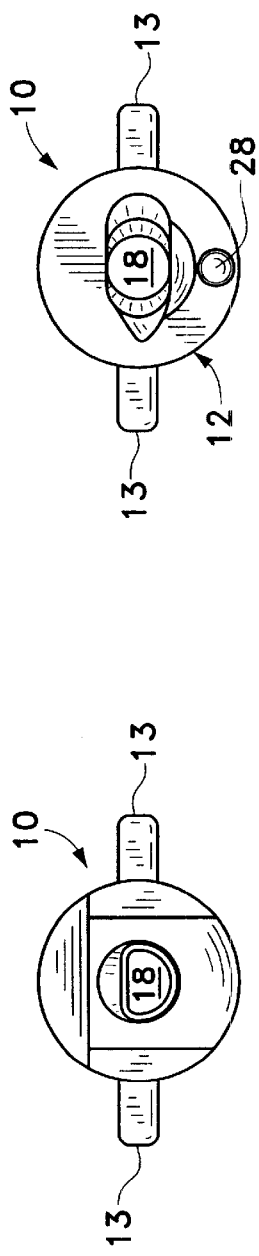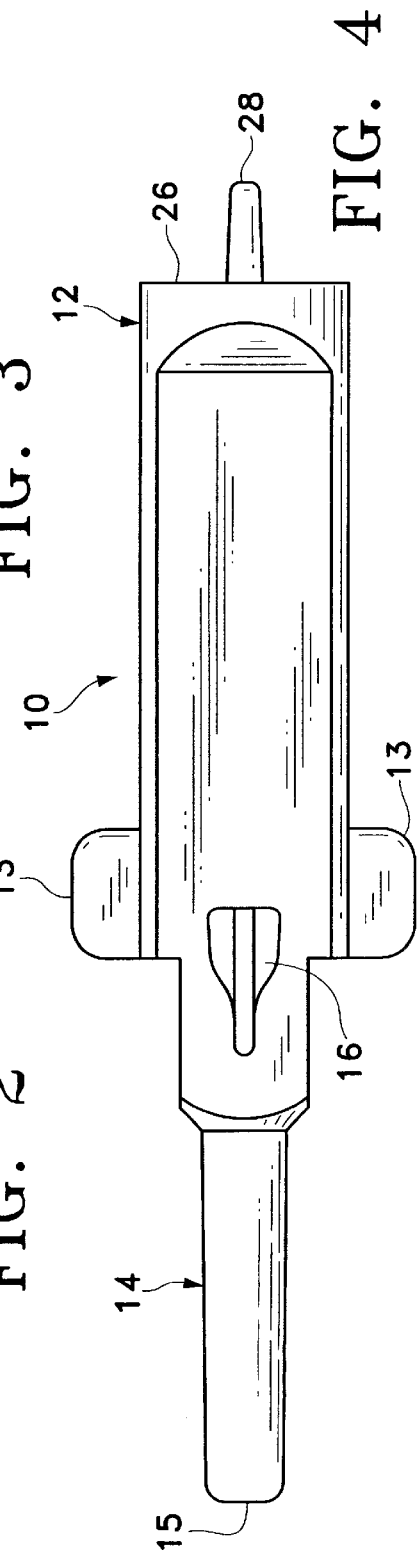

INTRAOCULAR LENS INJECTOR CARTRIDGE

This invention relates to intraocular lenses (IOLs) and more particularly to cartridges use to inject IOLs into an eye.

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in U.S. Pat. No. 4,681,102 (Bartell), and includes a split, longitudinally hinged cartridge. Similar designs are illustrated in U.S. Pat. Nos. 5,494,484 and 5,499,987 (Feingold) and U.S. Pat. Nos. 5,616,148 and 5,620,450 (Eagles, et al.), the entire contents of which are incorporated herein by reference. In an attempt to avoid the claims of U.S. Pat. No. 4,681,102, several solid cartridges have been investigated, see for example U.S. Pat. No. 5,275,604 (Rheinish, et al.), U.S. Pat. No. 5,653,715 (Reich, et al.) and U.S. Pat. No. 5,947,876 (Van Noy, et al.), the entire contents of which are incorporated herein by reference.

Viscoelastic lens materials, such as soft acrylics, are temperature sensitive, and roll or fold more easily at higher temperature. None of the prior art cartridges contain a feature that allows for the heating of the cartridge so as to warm the lens during insertion.

Accordingly a need continues to exist for a cartridge that allows for the heating of the cartridge so as to warm the lens during insertion.

BRIEF SUMMARY OF THE INVENTION

The present invention improves upon prior art lens injector cartridges by providing a cartridge having a heat retention additive for helping the cartridge retain heat after the cartridge is warmed. Such additives can include any biocompatible material having high heat retention, for example, powdered gold.

It is accordingly an object of the present invention to provide a lens injector cartridge that folds more easily a lens made from a soft acrylic.

It is a further object of the present invention to provide a lens injector cartridge that gently folds a soft acrylic lens.

Other objectives, features and advantages of the present invention will become apparent with reference to the drawings, and the following description of the drawings and claims.

BRIEF DESCRIPTION OF THE DRAWINGS

FIG. 1 is a side elevational view of an intraocular lens injector cartridge that may be used with the present invention.

FIG. 2 is a front elevational view of an intraocular lens injector cartridge that may be used with the present invention.

FIG. 3 is a rear elevational view of an intraocular lens injector cartridge that may be used with the present invention.

FIG. 4 is a top plan view of an intraocular lens injector cartridge that may be used with the present invention.

DETAILED DESCRIPTION OF THE INVENTION

As best seen in FIGS. 1–4, intraocular lens injector cartridge 10 suitable for use with the present invention generally has tubular body 12 and nozzle 14. Cartridge 10 is preferably molded as a single piece from any suitable thermoplastic, such as polypropylene. Nozzle 14 preferably is round or oval in cross-section, and distal tip 15 preferably is rounded on the interior and exterior. Body 12 preferably contains grips 13 that allow for easier manipulation of cartridge 10 and provide a locking mechanism for cartridge 10 within the handpiece (not shown). Body 12 may contain window or opening 16 that communicates with bore 18 and allows for visualization of the IOL (not shown). Proximal end 26 may contain peg 28 around which the haptic of the IOL (not shown) may be wrapped.

The material used to mold cartridge 10 preferably contains a heat retention agent. Any suitable, biocompatible material having a high heat capacitance may be used, for example, powdered gold. Cartridges 10 having such a heat retention agent may be warmed prior to the introduction of an IOL, for example, by bathing cartridge 10 in warm, sterile saline solution. The heat retention agent helps cartridge 10 retain the heat and transfer the heat to an IOL during insertion While certain embodiments of the present invention have been described above, these descriptions are given for purposes of illustration and explanation. Variations, changes, modifications and departures from the systems and methods disclosed above may be adopted without departure from the scope or spirit of the present invention.

I claim:

1. An intraocular lens injection cartridge comprising:

a) a body; and b) an injection nozzle integrally formed with the body, wherein the cartridge is molded from a thermoplastic containing a heat retention agent.

2. The cartridge of claim 1 wherein the thermoplastic is polypropylene.

3. The cartridge of claim 1 wherein the heat retention agent is powdered gold.

4. An intraocular lens injection cartridge comprising:

a) a body; and b) an injection nozzle integrally formed with the body, wherein the cartridge is molded from polypropylene containing powdered gold.

* * * * *